United States Patent
He et al.

(10) Patent No.: US 12,214,312 B2
(45) Date of Patent: Feb. 4, 2025

(54) DEHUMIDIFIER AND DEHUMIDIFICATION SYSTEM

(71) Applicant: Honeywell Analytics Inc., Charlotte, NC (US)

(72) Inventors: Xiangcai He, Shenzhen (CN); Xiufeng Tan, Shanghai (CN); Yuhui Xu, Shanghai (CN); Chuang Huang, Shanghai (CN)

(73) Assignee: Honeywell Analytics Inc., Charlotte, NC (US)

( * ) Notice: Subject to any disclaimer, the term of this patent is extended or adjusted under 35 U.S.C. 154(b) by 258 days.

(21) Appl. No.: 17/817,521

(22) Filed: Aug. 4, 2022

(65) Prior Publication Data
US 2023/0059257 A1 Feb. 23, 2023

(30) Foreign Application Priority Data

Aug. 18, 2021 (CN) .......................... 202110948908.5

(51) Int. Cl.
*B01D 53/26* (2006.01)
*G01N 33/00* (2006.01)

(52) U.S. Cl.
CPC ......... *B01D 53/261* (2013.01); *B01D 53/265* (2013.01); *G01N 33/0006* (2013.01); *G01N 33/0072* (2024.05)

(58) Field of Classification Search
None
See application file for complete search history.

(56) References Cited

U.S. PATENT DOCUMENTS

| 4,738,693 A * | 4/1988 | Tom .................. B01D 53/0446 96/108 |
| 5,873,252 A * | 2/1999 | Springmann ........ B01D 53/002 62/3.4 |
| 5,893,408 A * | 4/1999 | Stark ........................ F24F 3/14 62/93 |

(Continued)

FOREIGN PATENT DOCUMENTS

| FR | 1166596 A | 11/1958 |
| KR | 10-2018-0080752 A | 7/2018 |

OTHER PUBLICATIONS

European Search Report received for European Patent Application No. 22188706, mailed on Jan. 5, 2023, 7 pages.

(Continued)

*Primary Examiner* — Patrick Assouad
*Assistant Examiner* — Mark A Shabman
(74) *Attorney, Agent, or Firm* — Alston & Bird LLP

(57) ABSTRACT

The present application discloses a dehumidifier and a dehumidification system. The dehumidifier comprises a housing and a water absorber located in the housing. An opening and a plug are provided at a lower portion of the housing. The plug is used to seal the opening, and the water absorber can be removed via the opening when the opening is open. A conduit is provided above the housing, an upper gas inlet and an upper gas outlet are provided on the conduit, a gas to be dehumidified enters the conduit via the upper gas inlet and is discharged from the conduit via the upper gas outlet, and the water absorber is used to absorb water in the gas. The dehumidifier according to the present application is easily maintainable.

13 Claims, 4 Drawing Sheets

(56) References Cited

U.S. PATENT DOCUMENTS

2011/0232485 A1* 9/2011 Ellsworth ................ B32B 3/26
  95/91
2019/0274588 A1 9/2019 Cardin

OTHER PUBLICATIONS

Decision to grant a European patent Mailed on May 24, 2024 for EP Application No. 22188706, 2 page(s).
Communication about intention to grant a European patent Mailed on Jan. 24, 2024 for EP Application No. 22188706, 6 page(s).

* cited by examiner

DEHUMIDIFIER AND DEHUMIDIFICATION SYSTEM

CROSS-REFERENCE TO RELATED APPLICATIONS

This application claims priority pursuant to 35 U.S.C. 119(a) to Chinese Application No. 202110948908.5, filed Aug. 18, 2021, which application is incorporated herein by reference in its entirety.

TECHNICAL FIELD

The present application relates to the field of dehumidification, and in particular to a dehumidifier and a dehumidification system provided with such a dehumidifier.

BACKGROUND

Typically, a gas detector is calibrated using a dry standard gas. However, when the gas detector is used to perform detection on a gas, moisture in the gas to undergo detection may adversely affect the detection, for example affecting the stability, accuracy and service life of the gas detector. Therefore, the gas needs to be dehumidified before undergoing detection performed by the gas detector.

SUMMARY

A major technical problem to be solved by the present application is to provide an easily maintainable dehumidifier.

To address the above-mentioned technical problem, the present application provides a dehumidifier, comprising a housing and a water absorber located in the housing, wherein an opening and a plug are provided at a lower portion of the housing, the plug is used to seal the opening, the water absorber can be removed via the opening when the opening is open, a conduit is provided above the housing, an upper gas inlet and an upper gas outlet are provided on the conduit, a gas to be dehumidified enters the conduit via the upper gas inlet and is discharged from the conduit via the upper gas outlet, and the water absorber is used to absorb water in the gas.

In addition, the present application provides a dehumidification system comprising the above-mentioned dehumidifier, and the dehumidification system is used in a gas detector.

According to the technical solution of the present application, the water absorber is provided in the housing and is used to absorb and store the water removed from the gas, and the opening and the plug for sealing the opening are provided at a lower portion of the housing. After the dehumidifier is used for a period of time, the plug is removed, so as to remove the old water absorber via the opening and to put in a new water absorber, thereby facilitating maintenance.

BRIEF DESCRIPTION OF THE DRAWINGS

The disclosure of the present application is illustrated with reference to the accompanying drawings. It should be understood that the drawings are for illustrative purposes only, and are not intended to constitute a limitation on the scope of protection of the present application. In the drawings, unless otherwise stated, the same reference numerals are used to denote the same components. Herein.

DETAILED DESCRIPTION OF THE EMBODIMENTS

Figure 1:
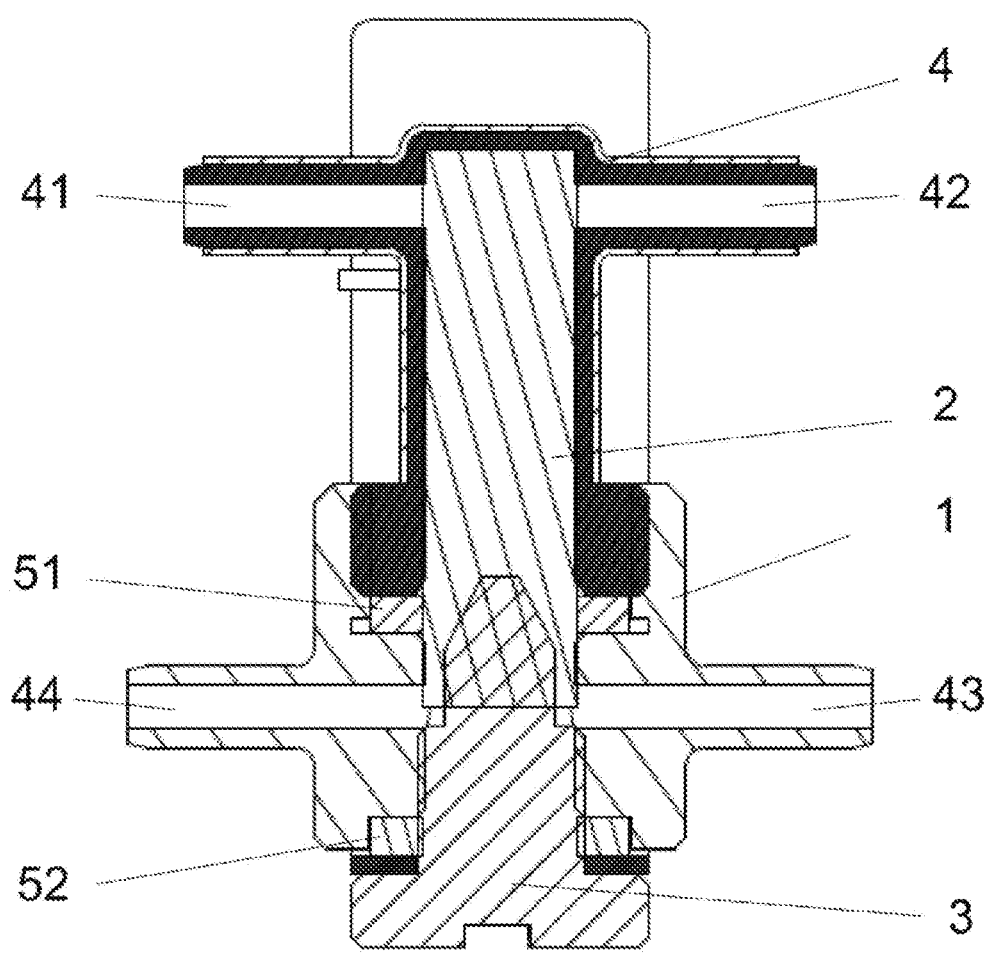
FIG. 1 schematically shows a cross-section of a dehumidifier according to an embodiment of the present application at a viewing angle.
Figure 2:
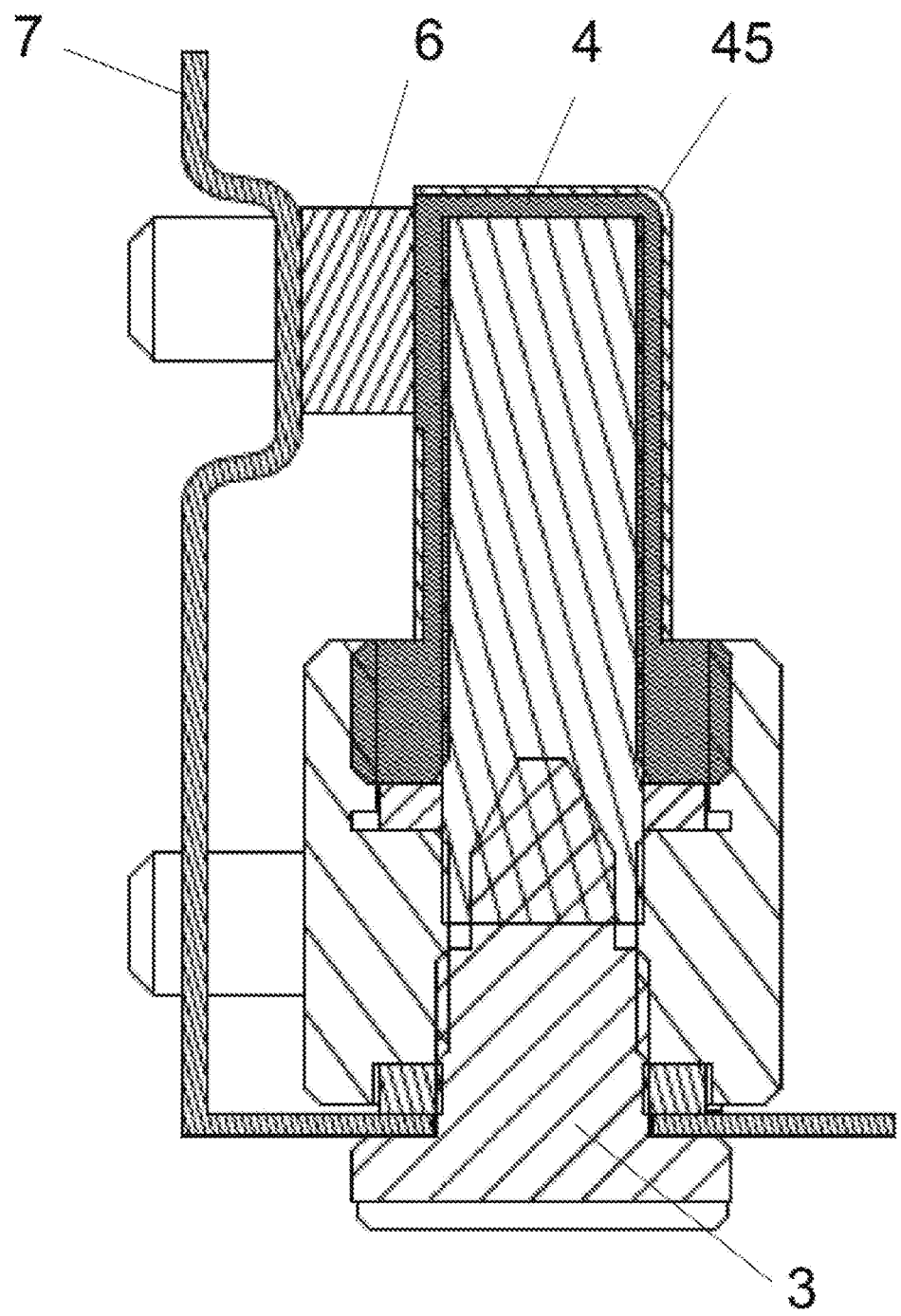
FIG. 2 schematically shows a cross-section of the dehumidifier in FIG. 1 at another viewing angle.
Figure 3:
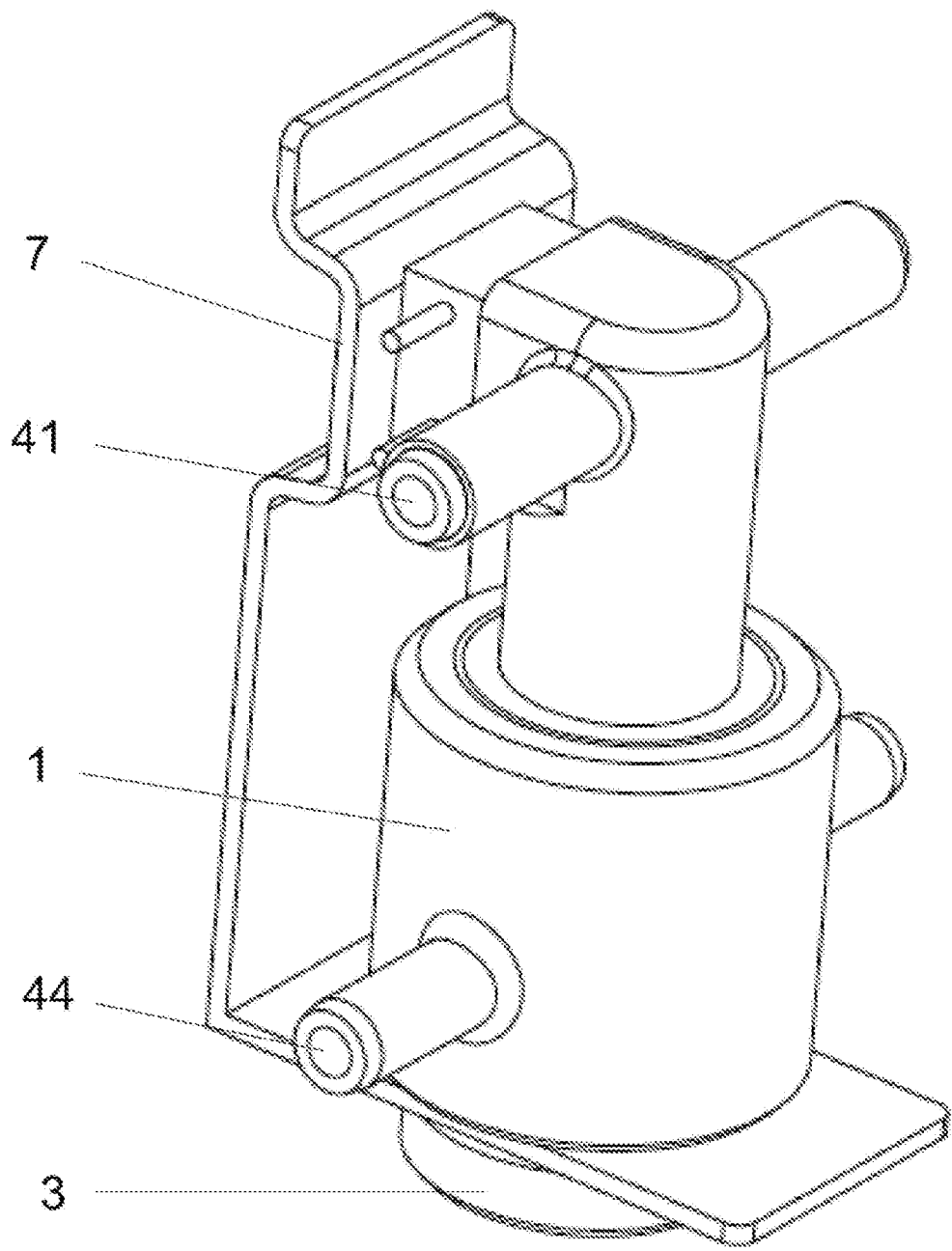
FIG. 3 schematically shows the dehumidifier in FIG. 1 in a perspective view.

Referring to FIGS. 1 to 3, a dehumidifier according to a specific embodiment of the present application comprises a housing 1 and a water absorber 2 located in the housing. The water absorber is used to absorb water, and is, for example, configured as a water absorbing foam. An opening and a plug 3 are provided at a lower portion of the housing. The plug is used to seal the opening, and the water absorber can be removed via the opening when the opening is open. For example, the plug is configured as a bolt, an external thread of the bolt matches an internal thread configured to be in the opening such that the plug can be screwed into the opening and seal the opening, and the water absorber can be removed or installed by unscrewing the plug.

A conduit is provided above the housing, an upper gas inlet 41 and an upper gas outlet 42 are provided on the conduit, a gas to be dehumidified enters the conduit via the upper gas inlet and is discharged from the conduit via the upper gas outlet, and the water absorber is used to absorb water in the gas. The conduit is a condensing tube or the conduit comprises a condensing tube, and the water absorber is used to absorb condensed water obtained via the condensing tube.

In the embodiment shown in the figures, a condensing tube 4 is provided above the housing, and the water absorber is used to absorb condensed water obtained via the condensing tube. The water absorbent fills, for example, a space in the condensing tube, and the plug is, for example, partially pressed into the water absorber so as to increase a filling degree of the water absorber. A thermal insulation foam 45 is provided on the outermost side of the condensing tube and is used to prevent heat exchanges between the condensing tube and the surrounding environment. The condensing tube is refrigerated, such that a gas flowing through the condensing tube is cooled by the condensing tube, and water contained in the gas is condensed into a liquid state and then absorbed by the water absorber and stored therein.

In the dehumidifier, the water absorber is provided in the housing and is used to absorb and store the water removed from the gas, and the opening and the plug for sealing the opening are provided at a lower portion of the housing. After the dehumidifier is used for a period of time, for example, before saturation of the water absorber, the plug is removed, so as to remove the old water absorber via the opening and to put in a new water absorber, thereby facilitating maintenance of the dehumidifier and ensuring the dehumidification performance of the dehumidifier. In addition, if there is liquid water stored in the water absorber, some water-soluble components in the gas will be absorbed by the water in the water absorber and thus stored in the water absorber, which is particularly advantageous when these water-soluble components are not needed. For example, when the dehumidifier is used in a gas detector, the water-soluble components may interfere with detection results. On the one hand, absorption and storage of the water-soluble components by the water absorber can prevent interference thereof with the detection results; and on the other hand, timely replacement of the water absorber can prevent the gas that has undergone detection the previous time from interfering with a subsequent detection.

In the embodiment shown in the figures, a semiconductor refrigeration chip 6 is provided outside the condensing tube. The semiconductor refrigeration chip employs the Peltier effect so that when the semiconductor refrigeration chip is energized, a heating end of the semiconductor refrigeration chip emits heat and a refrigeration end of the semiconductor refrigeration chip absorbs the heat. The refrigeration end (on the right of the figure) of the semiconductor refrigeration chip is connected to the condensing tube. For example, the refrigeration end of the semiconductor refrigeration chip is in direct contact with the condensing tube, so that the condensing tube is cooled thereby and the condensing tube can thus condense water. The heating end (on the left of the figure) of the semiconductor refrigeration chip is connected to a thermal conductor 7 to dissipate heat, thereby increasing the refrigeration efficiency of the semiconductor refrigeration chip. The thermal conductor is, for example, configured to have a plate shape and is made from copper.

In the embodiment shown in the figures, the upper gas inlet 41 and the upper gas outlet 42 are provided on the condensing tube, and a gas to be dehumidified enters the condensing tube via the upper gas inlet and is discharged from the condensing tube via the upper gas outlet. In addition, a lower gas inlet 43 and a lower gas outlet 44 are provided on the housing, and a dehumidified gas enters the housing via the lower gas inlet and is discharged from the housing via the lower gas outlet, so as to take away at least part of water from the water absorber. The dehumidified gas passes, for example, through a gap in the water absorber so as to take away the water in the water absorber, and is discharged from the lower gas outlet.

The dehumidified gas may come from a gas flowing out of the upper gas outlet, and after being discharged from the upper gas outlet, flows into another device such as a gas detector, and then is discharged from the device and flows into the lower gas outlet; or the dehumidified gas may also come from a gas generated or discharged by the other device, thereby drying the water absorber specifically.

Further, heat generated by the heating end of the semiconductor refrigeration chip is conducted through the thermal conductor and used to heat the water absorber, so as to accelerate evaporation of the water in the water absorber and allow more water to be discharged via the lower gas outlet, thereby delaying saturation of the water absorber and reducing the replacement frequency of water absorbers as much as possible. In the figures, the thermal conductor is connected to the plug, and heats the plug first and then heats the water absorber through the plug, thereby providing a compact structure. In an embodiment not shown in the figures, the thermal conductor may also directly heat the water absorber. The plug may be fixedly connected to the water absorber. For example, the water absorber is engaged with the plug through an engagement member on the plug. When the plug is removed, the water absorber is brought out together, thereby omitting a step of removing the water absorber separately.

A seal 51 is provided between the housing 1 and the condensing tube 4, and a seal 52 is provided between the housing 1 and the plug 3. The seals 51 and 52 perform a sealing function so that an internal space formed by the plug, the housing and the condensing tube is isolated from the surrounding environment. In addition, the condensing tube is not in direct contact with the plug, and the seals 51 and 52 may also perform a thermal insulation function, thereby preventing heat exchanges between the condensing tube, the housing and the plug, particularly preventing heat exchanges between the condensing tube and the plug, and ensuring that respective functions of the cold condensing tube and the hot plug are not affected. The housing 1 is made from a material having good thermal insulation performance, e.g., a thermal insulation plastic material.

The present application further relates to a dehumidification system comprising the dehumidifier of any of the preceding embodiments. The dehumidification system is used in a gas detector, and specifically, the dehumidification system is used to dehumidify a gas to undergo detection.

According to an embodiment of the present application, the dehumidification system further comprises a first sensor located upstream of the dehumidifier and a second sensor located downstream of the dehumidifier, the first sensor and the second sensor being used to measure the temperature, humidity and pressure of a gas. For example, the first sensor is located before the upper gas inlet, and the second sensor is located behind the upper gas outlet. By comparing the measurement results of the first sensor and the first sensor, the dehumidification performance of the dehumidifier can be evaluated, and the dehumidifier is adjusted accordingly if necessary, such as adjusting the refrigeration power or replacing the water absorber.

According to an embodiment of the present application, the dehumidification system comprises a power source and an outer housing. The power source supplies power to a semiconductor refrigeration chip, and the outer housing provides insulation and protection for the dehumidification system. A first aperture is provided at a lower portion of the outer housing, and the first aperture of the outer housing corresponds to the opening of the housing. Specifically, the first aperture of the outer housing corresponds to the opening of the housing in size and position, so that the plug and the water absorber can be freely removed and installed.

Figure 4:
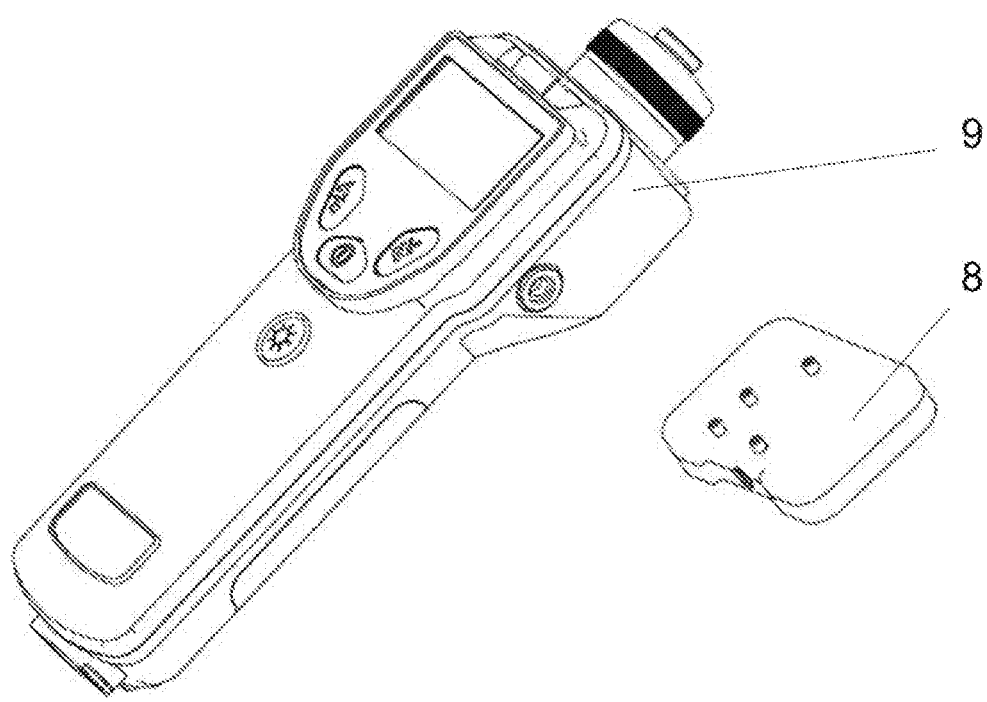
FIG. 4 schematically shows a dehumidification system and a gas detector according to an embodiment of the present application in a perspective view.

Referring to FIG. 4, a dehumidification system 8 can be configured as an independent module. When needed, the module can be connected to a gas detector 9 to dehumidify a gas to undergo detection; and when not needed, the module can be removed from the gas detector.

The upper gas inlet of the dehumidifier is connected to a first gas outlet of the gas detector, and a gas to be dehumidified enters the upper gas inlet of the dehumidifier through the first gas outlet of the gas detector and then is dehumidified. The upper gas outlet of the dehumidifier is connected to a first gas inlet of the gas detector, and the dehumidified gas enters the first gas inlet of the gas detector through the upper gas outlet of the dehumidifier and then undergoes detection in the gas detector. Further, the lower gas inlet of the dehumidifier is connected to a second gas outlet of the gas detector, and the gas that has undergone detection enters the lower gas inlet of the dehumidifier through the second gas outlet of the gas detector and then takes away part of the water in the water absorber; and the lower gas outlet of the dehumidifier is connected to a second gas inlet of the gas detector, so that the gas is introduced again into the gas detector.

In addition, the dehumidification system may comprise a pump, and the pump provides power to the flow of a gas. The dehumidification system may further comprise a second aperture, and the thermal conductor passes through the second aperture and is exposed to the surrounding environment, thereby accelerating heat dissipation of the thermal conductor.

The invention claimed is:

1. A dehumidifier for a gas detector, comprising a housing and a water absorber located in the housing, wherein an opening, a plug, and a first seal are provided at a lower portion of the housing, the plug and the first seal are used to seal the opening, the water absorber can be removed via the opening when the opening is open, a conduit is provided above the housing, an upper gas inlet and an upper gas outlet are provided on the conduit, a gas to be dehumidified enters the conduit via the upper gas inlet and is discharged from the conduit via the upper gas outlet, and the water absorber is used to absorb water in the gas, wherein the conduit is a condensing tube or the conduit comprises a condensing tube, and the water absorber is used to absorb condensed water obtained via the condensing tube, and wherein a second seal is provided between the housing and the condensing tube.

2. The dehumidifier according to claim 1, wherein a semiconductor refrigeration chip is provided outside the condensing tube, and a refrigeration end of the semiconductor refrigeration chip is connected to the condensing tube.

3. The dehumidifier according to claim 2, wherein a heating end of the semiconductor refrigeration chip is connected to a thermal conductor to dissipate heat, and heat generated by the heating end of the semiconductor refrigeration chip is conducted through the thermal conductor and used to heat the water absorber.

4. The dehumidifier according to claim 3, wherein the thermal conductor is connected to the plug and heats the water absorber through the plug.

5. The dehumidifier according to claim 1, wherein a lower gas inlet and a lower gas outlet are provided on the housing, and a dehumidified gas enters the housing via the lower gas inlet and is discharged from the housing via the lower gas outlet, so as to take away at least part of water from the water absorber.

6. The dehumidifier according to claim 1, wherein the plug is configured as a bolt and can be screwed into the opening, and/or the water absorber is configured as a water absorbing foam.

7. The dehumidifier according to claim 1, wherein the plug is fixedly connected to the water absorber.

8. A dehumidification system comprising the dehumidifier of claim 1, wherein the dehumidification system is used in a gas detector.

9. The dehumidification system according to claim 8, comprising a first sensor located upstream of the dehumidifier and a second sensor located downstream of the dehumidifier, the first sensor and the second sensor being used to measure the humidity of a gas.

10. The dehumidification system according to claim 8, comprising a power source and an outer housing, the power source supplying power to the semiconductor refrigeration chip, the outer housing providing insulation and protection for the dehumidification system, a first aperture being provided at a lower portion of the outer housing, and the first aperture of the outer housing corresponding to the opening of the housing.

11. The dehumidification system according to claim 10, comprising a second aperture, the thermal conductor passing through the second aperture and exposed to the surrounding environment.

12. The dehumidification system according to claim 8, wherein the upper gas inlet of the dehumidifier is connected to a first gas outlet of the gas detector, and the upper gas outlet of the dehumidifier is connected to a first gas inlet of the gas detector.

13. The dehumidification system according to claim 8, wherein a lower gas inlet of the dehumidifier is connected to a second gas outlet of the gas detector, and a lower gas outlet of the dehumidifier is connected to a second gas inlet of the gas detector.

* * * * *